United States Patent [19]
Griffin, III et al.

[11] Patent Number: 5,928,276
[45] Date of Patent: Jul. 27, 1999

[54] COMBINED CABLE AND ELECTROPHYSIOLOGY CATHETERS

[76] Inventors: Joseph C. Griffin, III; David A. Jenkins, both of 575 Rte. 73 North, Unit D, West Berlin, N.J. 08091-9293

[21] Appl. No.: 09/095,918

[22] Filed: Jun. 11, 1998

[51] Int. Cl.⁶ ...................................................... A61N 1/05
[52] U.S. Cl. ............................................................ 607/116
[58] Field of Search .................................... 600/373, 374, 600/376, 377, 381; 607/116, 117, 119, 122, 131, 36

[56] References Cited

U.S. PATENT DOCUMENTS

| | | | |
|---|---|---|---|
| 3,737,579 | 6/1973 | Bolduc | 607/131 |
| 3,913,587 | 10/1975 | Newash | 607/116 |
| 4,094,321 | 6/1978 | Muto | 607/38 |
| 5,092,333 | 3/1992 | Tsuchida et al. | 607/116 |

*Primary Examiner*—William E. Kamm
*Attorney, Agent, or Firm*—Norman E. Lehrer

[57] ABSTRACT

A single-use, disposable electrophysiology catheter having an elongated flexible tube with a proximal end and a distal end and a cable permanently secured to the proximal end via a connector is disclosed. The cable has a length of approximately four feet and is in the form of a folded ribbon, encased in a perforated plastic wrap until it is ready to be used. In this manner, the cable remains sterile until it is ready to be used. When the cable is needed, the wrap is torn along the perforation by pulling on the cable. The cable also has an adapter on its proximal end which may be used to attach an extension cable if a greater length is necessary.

7 Claims, 2 Drawing Sheets

COMBINED CABLE AND ELECTROPHYSIOLOGY CATHETERS

Background of the Invention

The present invention is directed toward the combination of an electrophysiology catheter and cable and more particularly, toward a cable permanently secured to the catheter where the cable is in a folded ribbon configuration until it is ready to be used.

Electrophysiology catheters are well known in the art and have been manufactured by a number of companies over the last thirty years or more. These catheters are designed with one or more electrodes at the distal end of the catheter and are generally independently wired so that each electrode will have an independent connector at the proximal end of the catheter. Alternatively, each of the electrodes may have its own conducting wire end in one multi-pin connector. In the latter case, the connector is designed to connect to a connecting cable which then has independent connectors at its opposite end. Most of these catheters connect to hardware devices that are some distance from the patient in which the catheter is used, so the connecting cable is necessary.

There are many shortcomings in using a connecting cable. For example, the cables are not generic, i.e., each catheter manufacturer has its own cable. Each type of catheter, such as a four-pin or a ten-pin will have a different cable. Therefore, if a manufacturer has three different catheters, it also has three different connecting cables. If it is anticipated that the physician will use two of the same catheter in one procedure, then two of each cable are necessary. If there are two procedures being performed in one day, the number of cables could again double because all of the cables must be sterile. If a facility uses several manufacturers with several catheters, it is not inconceivable to have fifty or sixty cables in inventory. These cables are expensive and bulky and each must be sterilized before each use.

The present invention is directed toward the elimination of separate connecting cables used on electrophysiology catheters by permanently fixing a cable onto the catheter. The cable is thin, yet flexible, non-bulky, and noise-free so the physician can still manipulate, torque, and turn the catheter without the interference of a bulky tail fixed to the catheter. Furthermore, the catheter and cable combination is used once and disposed of.

Summary of the Invention

The present invention is designed to overcome the deficiencies of the prior art discussed above. It is an object of the invention to provide a cable permanently secured to an electrophysiology catheter.

It is a further object of the present invention to provide the combination of a cable secured to an electrophysiology catheter where the cable is in a folded ribbon configuration until it is ready to be used.

In accordance with the illustrative embodiments, demonstrating features and advantages of the present invention, there is provided the combination of an electrophysiology catheter and a cable permanently secured thereto. The combination includes a catheter having an elongated flexible tube with a proximal end and a distal end; a cable permanently secured to the proximal end; and a handle for securing the cable to the tube. The cable is in the form of a folded ribbon and may be encased or wrapped in a piece of plastic before it is used.

Brief Description of the Drawings

For the purpose of illustrating the invention, there is shown in the accompanying drawings one form which is presently preferred; it being understood that the invention is not intended to be limited to the precise arrangements and instrumentalities shown.

Detailed Description of the Preferred Embodiment

Figure 1:
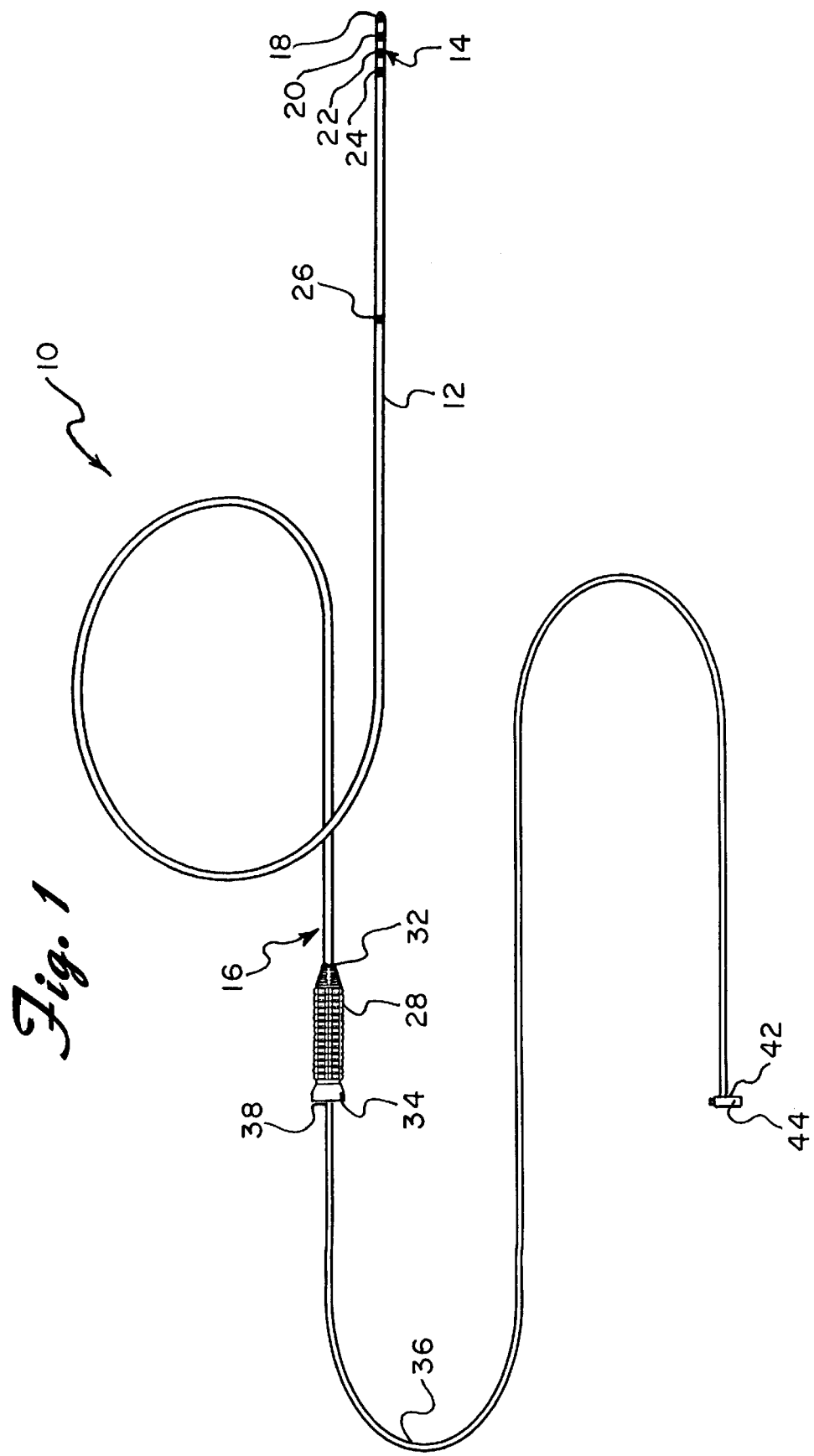
FIG. 1 is perspective view of the combination of the electrophysiology catheter and cable of the present invention.

Referring now to the drawings in detail wherein like reference numerals have been used throughout the various figures to designate like elements, there is shown in FIG. 1 the combination of an electrophysiology catheter and a cable secured thereto constructed in accordance with the principles of the present invention and designated generally as 10. Except in those areas which will become clear hereinafter, the electrophysiology catheter may be constructed in essentially the same manner as the electrode catheter described in the following co-pending applications: Ser. No. 08/751,436, filed on Nov. 20, 1996, now abandoned entitled "Temporary Atrial Defibrillation Catheter with Improved Electrode Configuration and Method of Fabrication;" Ser. No. 08/789,937, filed on Jan. 28, 1997, entitled "Focused Energy Array Ablation Catheter;" Ser. No. 08/818,408 filed on Mar. 14, 1997, entitled "Atrial Defibrillation Catheter;" and Ser. No. 08/885,501 filed on Jun. 30, 1997, now U.S. Pat. No. 5,888,577, entitled "Method for Forming an Electrophysiology Catheter." The subject matter of each of these co-pending applications, assigned to the present assignee, is incorporated herein by reference.

The combination of the catheter and cable 10 includes an electrophysiology catheter which includes an essentially electrically insulative catheter body comprising an elongated flexible member or tube 12. A preferred material for producing the flexible member 12 is extruded polyether block amide of the type sold by Atochem North America, Inc. under the trademark PEBAX. However, the flexible member 12 may be comprised of other polymeric materials which have excellent memory characteristics such as polyurethane, silicone rubber, and plasticized PVC.

The flexible member 12 has one central lumen (not shown) but it may also have more than one lumen in order to house bare copper wire, to infuse fluids, to sample blood, or to measure pressure. The conductor wire may also be made from stainless steel, platinum, gold, silver, or alloys thereof. The catheter may be of various diameters and sizes in order to accommodate various anatomical or manufacturing conditions. However, the preferred dimensions of the catheter are an outer diameter of 6 French (2mm) and a length of 110 cm.

The flexible member 12 has a deflectable distal end 14 and a proximal end 16. The distal end 14 may have one or more electrode sections. For example, the electrode sections may include mapping and stimulation electrodes 18, 20, 22, and 24 and a reference electrode 26. (See FIG. 1.) Extending through the flexible member 12 are conducting wires (not shown) which connect with the electrodes 18, 20, 22, 24, and 26. At the proximal end 16 of the flexible member 12, the ends of the conducting wires are soldered or otherwise connected to the conductors within the cable 36.

Figure 3:
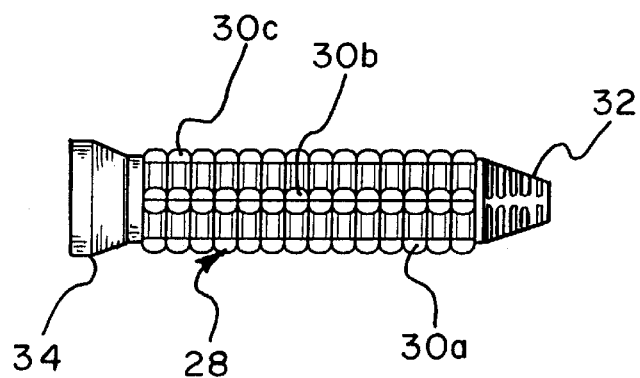
FIG. 3 is a perspective view of the handle of the present invention.

Secured to the proximal end 16 of the flexible member 12 is a rubber-like grip in the form of a handle 28. The handle 28 may be made from rubber, plastic, or any other flexible material generally known and used in the art. The handle 28 is in the form of a tube with a plurality of ridges, for example, 30*a–c*, and is molded around the connection between ends of the conducting wires within the catheter and the proximal ends of the conductors within the cable 36. The handle 28 also has a distal end 32 which is tapered slightly to grip the flexible member 12 and a proximal end 34 which is flared. (See FIG. 3.) The handle 28 protects the electrical connections.

Figure 2:
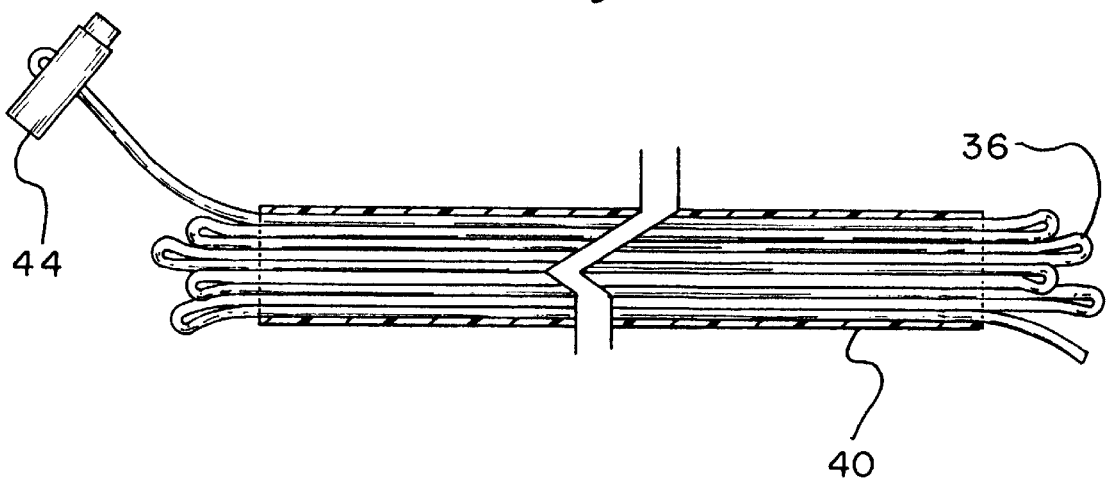
FIG. 2 is a partial, enlarged view of the cable of the present invention.

Extending proximally from the proximal end 34 of the handle 28 is the cable 36 in the form of a flexible ribbon which has a length of approximately four feet. The cable 36 is permanently connected to the catheter via the handle 28 at the distal end 38 of the cable 36. Furthermore, all of the wires that are within the catheter and extend outwardly from the proximal end 16 thereof are permanently secured to the cable 36. The cable 36 is folded about itself and then wrapped or encased with a piece of plastic 40 or like material. (See FIG. 2.) The plastic 40 may be perforated or otherwise have a frangible means which may be broken or opened when the cable 36 is pulled, thereby releasing the cable 36. At the proximal end 42 of the cable 36 is an adapter 44 which houses one or more pins (not shown) so that the cable 36 and catheter may be connected to particular instruments or to an extension cable, depending upon the length of the cable needed.

The cable 36 is permanently secured to the flexible member 12 of the catheter and is folded and wrapped in a piece or wrap of plastic 40 so that the catheter and cable can be made to be completely sterile. This is an advantage over the prior art because the catheter and cable are disposable and the cable need not be re-sterilized and re-used. That is, the catheter and cable are only used once and discarded. Also, if a longer cable is necessary, the adapter at the proximal end of the cable may be used to attach an extension cable. Sterilization of the extension cable is not necessary because the extension cable is attached at a location so remote from the immediate surgical area that the extension cable need not be sterile.

The present invention may be embodied in other specific forms without departing from the spirit or essential attributes thereof and accordingly, reference should be made to the appended claims rather than to the foregoing specification as indicating the scope of the invention.

We claim:

1. An electrophysiology catheter comprising:

an elongated flexible tube having a proximal end and a distal end;

a cable permanently secured to said proximal end, said cable being in the form of a folded ribbon; and.

connecting means for securing said cable to said elongated tube.

2. The catheter of claim 1 further including a wrap encasing said cable.

3. The catheter of claim 2 wherein said wrap is made from plastic.

4. The catheter of claim 3 wherein said wrap includes a frangible portion so that said cable can be quickly removed and unfolded.

5. The catheter of claim 1 wherein said connecting means is secured to said proximal end of said flexible tube.

6. The catheter of claim 5 wherein said connecting means is comprised from a rubber-like material.

7. The catheter of claim 1 wherein said cable has an adapter.

* * * * *